United States Patent
Doyle et al.

(10) Patent No.: US 9,256,029 B2
(45) Date of Patent: Feb. 9, 2016

(54) SURFACE-MOUNT CONNECTOR STRUCTURE FOR EMBEDDED OPTICAL AND ELECTRICAL TRACES

(71) Applicant: International Business Machines Corporation, Armonk, NY (US)

(72) Inventors: Matthew S. Doyle, Rochester, MN (US); Joseph P. Kuczynski, North Port, FL (US); Kevin A. Splittstoesser, Stewartville, MN (US); Timothy J. Tofil, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 6 days.

(21) Appl. No.: 14/460,405

(22) Filed: Aug. 15, 2014

(65) Prior Publication Data
US 2016/0011369 A1    Jan. 14, 2016

Related U.S. Application Data

(63) Continuation of application No. 14/328,160, filed on Jul. 10, 2014.

(51) Int. Cl.
*G02B 6/12* (2006.01)
*G02B 6/42* (2006.01)
(Continued)

(52) U.S. Cl.
CPC ............... *G02B 6/125* (2013.01); *G02B 6/132* (2013.01); *G02B 6/428* (2013.01); *G02B 6/4295* (2013.01); *H05K 3/4038* (2013.01); *G02B 2006/12104* (2013.01)

(58) Field of Classification Search
CPC ............ G02B 6/00; G02B 6/12; G02B 6/125; G02B 6/132; G02B 6/428
USPC .................................................... 385/14–16
See application file for complete search history.

(56) References Cited

U.S. PATENT DOCUMENTS 5,539,554 A    7/1996  Lebby et al.
7,033,084 B2   4/2006  Lappohn
(Continued)

FOREIGN PATENT DOCUMENTS

| EP | 1818701 A1 | 8/2007 |
| JP | 2006154109 A | 6/2006 |
| WO | 2006115192 A1 | 11/2006 |

OTHER PUBLICATIONS

Houbertz et al., "Optoelectronic printed circuit board: 3D structures written by two-photon absorption," SPIE Proceedings, Aug. 26, 2008, 13 pages, vol. 7053, © SPIE.

(Continued)

*Primary Examiner* — Akm Enayet Ullah
(74) *Attorney, Agent, or Firm* — Wood, Herron & Evans, LLP; Robert R. Williams

(57) ABSTRACT

A system for use with optical and electrical signaling is disclosed. The system may include a printed circuit board (PCB) that includes a plurality of layers vertically stacked between a first face and a second face and a first optical signal transmission path within a first internal layer of the plurality of layers. The PCB may also include an electrical signal transmission path and a via extending through the plurality of layers. The via may include a first reflective surface that is configured to reflect light between the first optical signal transmission path and an opening of the via on the first face and an electrically conductive material that is configured to electrically connect the electrical signal transmission path to a portion of the via on the first face.

5 Claims, 5 Drawing Sheets

(51) Int. Cl.
    *G02B 6/125* (2006.01)
    *H05K 3/40* (2006.01)
    *G02B 6/132* (2006.01)

(56) References Cited

U.S. PATENT DOCUMENTS

| | | |
|---|---|---|
| 7,118,293 B2 | 10/2006 | Nagasaka et al. |
| 7,320,593 B2 | 1/2008 | Ostler et al. |
| 7,346,242 B2 | 3/2008 | Morlion et al. |
| 7,362,926 B2 | 4/2008 | Umezawa |
| 7,529,448 B2 | 5/2009 | Chen et al. |
| 7,801,397 B2 | 9/2010 | Block et al. |
| 8,121,451 B2 | 2/2012 | Yamanouchi et al. |
| 8,315,491 B2 | 11/2012 | Hino et al. |
| 8,548,284 B2 | 10/2013 | Warashina et al. |
| 2013/0081666 A1 | 4/2013 | Yoon |
| 2013/0241042 A1 | 9/2013 | Kwon |

OTHER PUBLICATIONS

Immonen et al., "Development of Electro-Optical PCBs With Polymer Waveguides for High-Speed On-Board Optical Interconnects," Circuit World, pp. 104-112, vol. 38—Issue 3, © Emerald Group Publishing Limited DOI: 10.1108/03056121211250623.

Kash et al., "Optical PCB Overview," IBM Research, Nov. 2009, © 2009 IBM Corporation.

Wang et al., "Fully Embedded Board-Level Optical Interconnects From Waveguide Fabrication to Device Integration," Journal of Lightwave Technology, Jan. 15, 2008, pp. 243-250, vol. 26—Issue 2 DOI: 10.1109/JLT.2007.911115.

Weck et al., "Laser drilling of high aspect ratio holes in copper with femtosecond, picosecond and nanosecond pulses," Applied Physics A—Materials Science & Processing, Published online Oct. 25, 2007, pp. 537-543, vol. 90—Issue 3, Copyright Springer-Verlag 2007 DOI: 10.1007/s00339-007-4300-6.

Doyle et al., "Surface-Mount Connector Structure for Embedded Optical and Electrical Traces," U.S. Appl. No. 14/328,160, filed Jul. 10, 2014.

List of IBM Patents or Patent Applications Treated As Related.

100
PC Board and Electrical/
Optical Connector Structure
(Cross-Sectional View)

150
PC Board Electrical/Optical
Connector Structure
(Top View)

US 9,256,029 B2

SURFACE-MOUNT CONNECTOR STRUCTURE FOR EMBEDDED OPTICAL AND ELECTRICAL TRACES

BACKGROUND

The present disclosure generally relates to printed circuit boards (PCBs). In particular, this disclosure relates to optical and electrical connector structures embedded within a PCB.

A PCB may be used to mechanically support and electrically connect electronic components using conductive paths or signal traces etched from copper sheets laminated onto non-conductive substrates. Multiple copper/insulator layer pairs (cores) may be laminated together in the fabrication of the PCB. The number and arrangement of cores may be designed to fit the needs of a variety of applications.

Vertical interconnect structures (vias) may be used to interconnect conductive signal traces between various conductive layers within the PCB. Copper shapes or areas may be used for power and ground distribution to components on the PCB. The interconnect structures in the PCB may be designed to be physically and electrically compatible with the components the PCB may be used to interconnect.

SUMMARY

Various aspects of the present disclosure may be useful for providing, on a face of a printed circuit board (PCB), access to optical and electrical signals transmitted on optically and electrically conductive layers, respectively, within the PCB. A surface-mount connector structure configured according to embodiments of the present disclosure may allow dense, high-bandwidth interconnections, which may be compatible with existing electronic module footprints, to optical and electrical signals transmitted within a PCB.

Embodiments may be directed towards a system for use with optical and electrical signaling. The system may include a PCB, which may include a plurality of layers vertically stacked between a first face and a second face, and a first optical signal transmission path within a first internal layer of the plurality of layers. The PCB may also include an electrical signal transmission path and a via extending through the plurality of layers. The via may include a first reflective surface that is configured to reflect light between the first optical signal transmission path and an opening of the via on the first face and an electrically conductive material that is configured to electrically connect the electrical signal transmission path to a portion of the via on the first face.

Embodiments may also be directed towards a method for forming a system for use with optical and electrical signaling in a PCB that includes a plurality of layers vertically stacked between a first face and a second face, a first optical signal transmission path within a first internal layer of the plurality of layers and an electrical signal transmission path. The method may include creating an opening in the PCB that intersects the first optical signal transmission path and the electrical signal transmission path and depositing an electrically conductive and optically reflective material in the opening. The method may also include removing an inner portion of the electrically conductive and optically reflective material to form a reflective surface that is configured to reflect light between the optical signal transmission path and an opening of the via on the first face. The method may also include removing an outer portion of the electrically conductive material from the via to allow light from the optical signal transmission path to reach the reflective surface, while leaving a portion of the conductive material in the via in contact with the electrical signal transmission path.

Aspects of the various embodiments may be used to provide adjacent or grouped optical and electrical interconnect structures for groups of signals with related functions. Aspects of the various embodiments may also be useful for providing cost-effective interconnect structures for use with PCBs, by using existing and proven fabrication, machining and PCB technologies.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
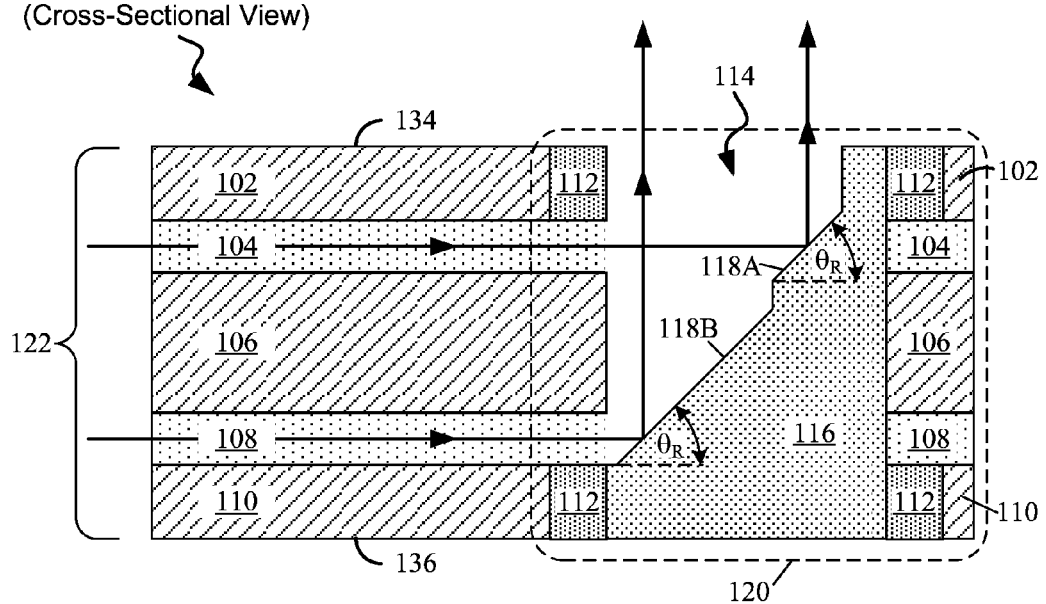
FIG. 1 includes a cross-sectional view and a top view depicting a printed circuit board (PCB) including an optical/electrical connector structure, according to embodiments of the present disclosure.
Figure 1:
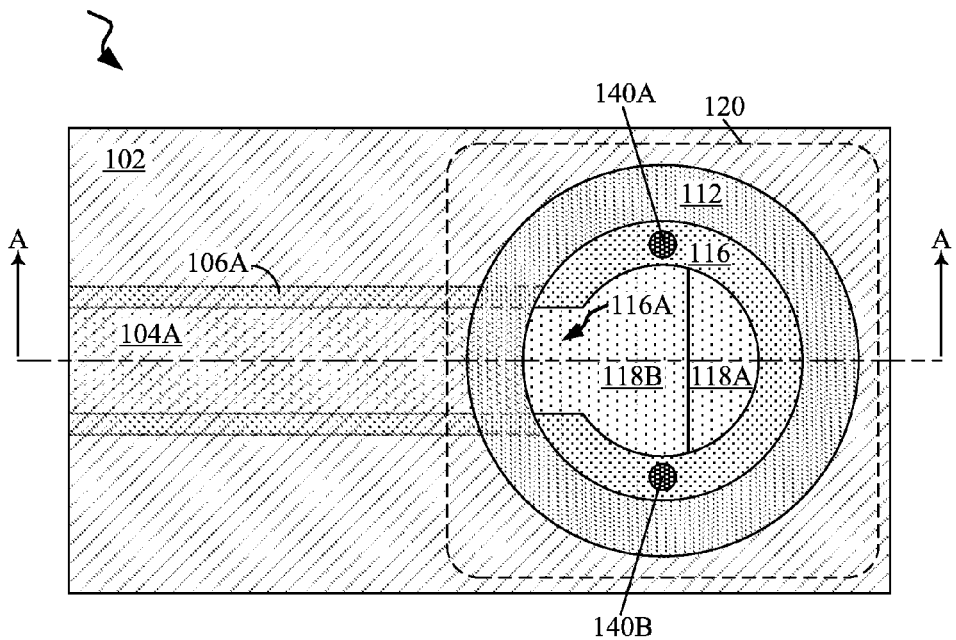

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

In the drawings and the Detailed Description, like numbers generally refer to like components, parts, steps, and processes.

DETAILED DESCRIPTION

Certain embodiments of the present disclosure can be appreciated in the context of connector structures that provide access, on a surface of a printed circuit board (PCB), to optical and electrical signal transmission paths within the PCB, which may be used to interface optical/electrical connectors to the PCB. Such connectors may include devices such as optical drivers, optical receivers and compressible electrical contacts. While not necessarily limited thereto, embodiments discussed in this context can facilitate an understanding of various aspects of the disclosure. Certain embodiments may also be directed towards other equipment and associated applications, such as connector structures that provide an optical/electrical interface, on a printed circuit board (PCB) surface to electro-optical components. Electro-optical components may be used in a wide variety of high-bandwidth computational, data processing, networking and telecom applications, and may include a planar array of electro-optical connectors. Such applications may include, but are not limited to, supercomputers, high-performance computing (HPC) systems, network switching systems and other types of special-purpose computers. Embodiments may also be directed towards electro-optical interfacing of a first PCB located in a perpendicular orientation to a second PCB, which may provide a compact, high-bandwidth optical interface between the PCBs.

For ease of discussion, the term "optical receiver" is used herein, in the context of an electronic device designed to receive and convert signals transmitted optically, through optical conductor layers within a PCB, into electrical signals. However, it is understood that various embodiments can also be useful with regards to optical transmitters which may be used to convert electrical signals into optical signals which are then transmitted through optical conductor layers within a PCB. The term "optical module" may be used herein to describe an electronic device which may be, in certain embodiments, an optical receiver, and in certain embodiments, an optical transmitter.

Various embodiments of the present disclosure relate to a dual optical/electrical connector structure that is configured to provide access to optically and electrically conductive layers within a printed circuit board (PCB). The connector structure may therefore be useful for connecting electrical and electro-optical devices, mounted on a face of a PCB, to optical and electrical signal transmission paths formed on the electrically and optically conductive layers within the PCB.

High density, high-bandwidth interconnection of electronic and electro-optical devices may result from the use of a dual optical/electrical connector structure. A dual optical/electrical connector structure may enable functionally related groups of optical and electrical signals to be accessed in a local grouping, which may increase performance and decrease design complexity of various electronic system implementations using a combination of electrically and optically transmitted signals.

An optical/electrical connector structure designed according to certain embodiments may be compatible with existing and proven printed circuit boards, electronic packaging and other electronic hardware, and may be useful in providing integrated, high-performance electro-optical interconnect solutions. And optical/electrical connector structure constructed according to embodiments of the present disclosure may be designed into PCBs fabricated using existing material sets and fabrication technologies.

In certain applications, digital optical signaling interconnects may have a higher usable bandwidth than electrical signaling interconnects. For example, an optical link may achieve serial data bandwidths of 28-40 gigabits per second (Gbps) for a particular optical conductor length, while a comparable electrical link may achieve serial data bandwidths of 12-15 gigabits per second (Gbps) for a similar electrical conductor length. High optical signaling bandwidths may have advantages in certain applications such as high-speed serial (HSS) data buses.

In certain applications, combining, in close proximity, functionally related optical and electrical interconnects may have advantages over "segregated" optical and electrical interconnects. For example, optical interconnections may be used for high-speed serial data transfer, while a functionally related electrical signal, e.g., a control or feedback signal, may be used to enable, disable or pause the high-speed optical interconnect. Arranging these two types of signals in close proximity may provide design and functional advantages in a particular electronic system. For example, input/output (I/O) devices on a chip or electronic module for both optical and electrical links may be grouped in close proximity, which may enable higher performance and/or ease of design.

PCB may include both optically and electrically conductive layers, and connectors to allow access to both types of layers may be designed into the PCB. Optical connector structures may allow access to optical signal transmission paths (within the PCB internal layers) at both the edge and on one or more faces of the PCB. Similarly, electrical connector structures may allow access to electrical signal transmission paths (within the PCB internal layers) on one or more faces of the PCB.

Certain embodiments relate to a system that includes a connector structure for providing access, on a face of a PCB, to both optical and electrical signal transmission paths within the PCB. FIG. 1 includes a cross-sectional view 100 and a top view 150 depicting a PCB 122 including an optical/electrical connector structure 120 configured to provide surface-mount access to optical and electrical signal transmission paths within the PCB 122, according to embodiments of the present disclosure. The connector structure 120 may be compatible with existing PCB material sets and fabrication technologies, and may be useful in enabling compact, high bandwidth optical and electrical connections, through a PCB, to connectors, components and other PCBs mounted on a surface of the PCB 122. Connector structure 120 may also be useful in providing small, high-density connections that are compatible with existing PCB connector structures such as vias and surface-mount pads.

According to embodiments, local access, through one connector structure, to two modes of signals (optical and electrical) transmitted through a PCB 122 may be useful when the signals are used in conjunction with one another. For example, optical signals may be used to transmit serial data from a first location on a PCB to a second location on the PCB. A related electrical signal, for example, accessed through the same connector structure as the optical signals, may be used for handshaking, data flow control, or to report bit errors to an optical transmitter circuit.

View 100 is a cross-section of a PCB 122 and an embedded optical/electrical connector structure 120, the PCB being sectioned along line A-A of view 150 (FIG. 1). The optical/electrical connector structure 120 is formed in a via opening 114 that extends through a plurality of layers vertically stacked between a first face 134 and a second face 136 of the PCB 122.

The plurality of layers includes metal layer 102, optical conductor layer 104, metal layer 106, optical conductor layer 108 and metal layer 110. The optical/electrical connector structure 120 includes electrically conductive and optically reflective material 116 and dielectric 112, which may surround material 116 on the (outer) metal layers 102 and 110 of the PCB 122. In certain embodiments, metal layers 102 and 110 may be used to supply power to, or provide a current return path (ground) for components mounted on the PCB. Dielectric 112 may be used to electrically insulate metal layers 102 and 110 from electrically conductive material 116.

Metal layer 106 may include an electrical signal transmission path, which may be used to transmit electrical signals from a first location of the PCB to a second location on the PCB. Metal layer 106 may be electrically connected to electrically conductive and optically reflective material 116. Metal layers 102, 106 and 110 and electrically conductive material 116 may include copper or copper alloys, consistent with current PCB material sets.

According to embodiments, a first internal layer of the plurality of layers, e.g., optical conductor layer 104, may contain a first optical signal transmission path. An optical signal transmission path may be a formed shape of optical material used to transmit and direct optical signals from a first location of the PCB to a second location on the PCB, for example, between an optical transmitter module and an optical receiver module. In certain embodiments, an optical signal may include high-speed serial (HSS) data, for example, at data rates of 40 gigabits per second (Gbps). Other types of data, at other data rates, may be transmitted across an optical signal transmission path.

In certain embodiments, a second internal layer (e.g., 108) of the plurality of layers may contain a second optical signal transmission path. Embodiments may have a plurality of optically conductive layers, based on a number of optical signal transmission paths included in a particular application. Optical and electrical signal transmission paths may be arranged in a variety of ways within a PCB, according to a signal transmission scheme of a particular application. For example, in certain embodiments, the first internal layer of the plurality of layers may contain an electrical signal transmission path that is adjacent to the first optical transmission path. In certain embodiments, a second internal layer adjacent to (i.e., above or below) the first internal layer may contain an electrical signal transmission path.

The optically conductive layers 104, 108 may be constructed from materials such as acrylics, polycarbonate, and a variety of other optically transparent polymers. The dimensions and optical properties of the optical material may be chosen to create an optical channel suitable to particular wavelength(s) of light transmitted across the optical channel.

In embodiments, via opening 114 may have a diameter corresponding to via sizes available in a given PCB technology. For example, in certain embodiments, via opening 114 may have a diameter of 10 mils, in certain embodiments a diameter of 20 mils, and in certain embodiments a diameter of 25 mils. A via opening 114 diameter may be chosen based upon a particular optical/electrical connector structure density, a size of an optical receiver or transmitter module or a selection of via diameters available in a particular technology.

Electrically conductive and optically reflective material 116 may be configured to electrically connect an electrical signal transmission path to a portion of the connector structure 120 on the first face of the PCB. Material 116 may include copper, copper alloys, or another material that is sufficiently electrically conductive and optically reflective to transmit electrical signals and reflect optical signals. Material 116 may include a first reflective surface 118A, and a second reflective surface 118B. Reflective surfaces 118A, 118B may be configured to reflect light transmitted through the first and second optical signal transmission paths on layers 104, 108, respectively, to a via opening 114 on the first face 134 of the PCB. Reflecting light off of reflective surfaces 118A, 118B to a via opening 114 may be useful in directing optical signals to an optical receiver, mounted on face 134 of the PCB, which may convert the optical signals into electrical signals, for use by another device.

Reflective surfaces 118A and 118B may be formed having a reflective surface angle $\theta_R$, relative to light transmitted by the optical signal transmission paths within layers 104, 108, respectively, of the PCB. Angle $\theta_R$ may be sufficient to reflect light transmitted from the first and second optical signal transmission paths 104, 108 to an opening of the via 114 on the first face 134. In certain embodiments, angle $\theta_R$ may be 45° for reflective surfaces 118A, 118B. In certain embodiments, angle $\theta_R$ may be different than 45° for either or both reflective surfaces 118A, 118B. By way of example, angle $\theta_R$ may be 50° in an embodiment having an optical receiver mounted in an orientation offset from a normal to the first face 134.

In embodiments, the angle $\theta_R$ of reflective surface 118A may be different than the angle $\theta_R$ of reflective surface 118B. For example, the two reflective surfaces 118A and 118B may be oriented at different angles $\theta_R$ which may be useful for reflecting light transmitted through two optical conductor layers 104, 106 onto a single optical receiver. Certain embodiments may include one reflective surface (e.g., 118A), and certain embodiments may include three reflective surfaces. A number of reflective surfaces in an embodiment may correspond to a number of optical conductor layers (e.g., 104), and may be limited by via 114 opening size, and corresponding number of optical receivers/transmitters which may be positioned to receive signals reflected off the reflecting surfaces, e.g, 118A, 118B.

According to embodiments, view 100 depicts two optical conductor layers (104, 108) which may be used for optical signal transmission paths, and one metal layer 106 which may be used for an electrical signal transmission path. View 100 is not limiting; embodiments may have a different number of optical conductor layers and metal layers useful for signal transmission paths, for particular applications. For example, certain embodiments may include two metal layers and three optical conductor layers, and certain embodiments may include four metal layers and four optical conductor layers.

View 150 depicts a top view of the PCB optical/electrical connector structure 120 consistent with view 100. Optical signal transmission path 104A may be formed within optical conductor layer 104 (view 100), and may be used as an optical channel between connector structure 120 and another connector structure, component, or location on the PCB. Similarly, electrical signal transmission path 106A may be formed within electrical conductor layer 106 (view 100), and may be used as an electrical conductor between connector structure 120 and another connector structure, component, or location on the PCB. Electrical signal transmission path 106A may be electrically connected to electrically conductive and optically reflective material 116.

Area 116A depicts a location where an outer portion of electrically conductive material 116 may be removed adjacent to an end of the optical signal transmission path 104A. Removal of material 116 in this area may allow light transmitted through optical transmission path 104A to enter via opening 114 (view 100), and subsequently be reflected off of a reflective surface (118A or 118B) to an opening of via 114 at the first face 134 of PCB 122. Electrically conductive material 116 (view 150) depicts a circumferential region of material that may be substantially flush with the first face 134 and the second face 136 of the PCB 122, which may be useful as an electrical contact point for connectors that mate with connector structure 120. Locations 140A, 140B, on conductive material 116 may indicate a location, when engaged, of a compressible electrical contact, which may be part of a connector 230 (FIG. 2), and which may mate with the connector structure 120 depicted in views 100, 150. Dielectric material 112 may be used to insulate metal layer 102 from electrically conductive material 116.

Figure 2:
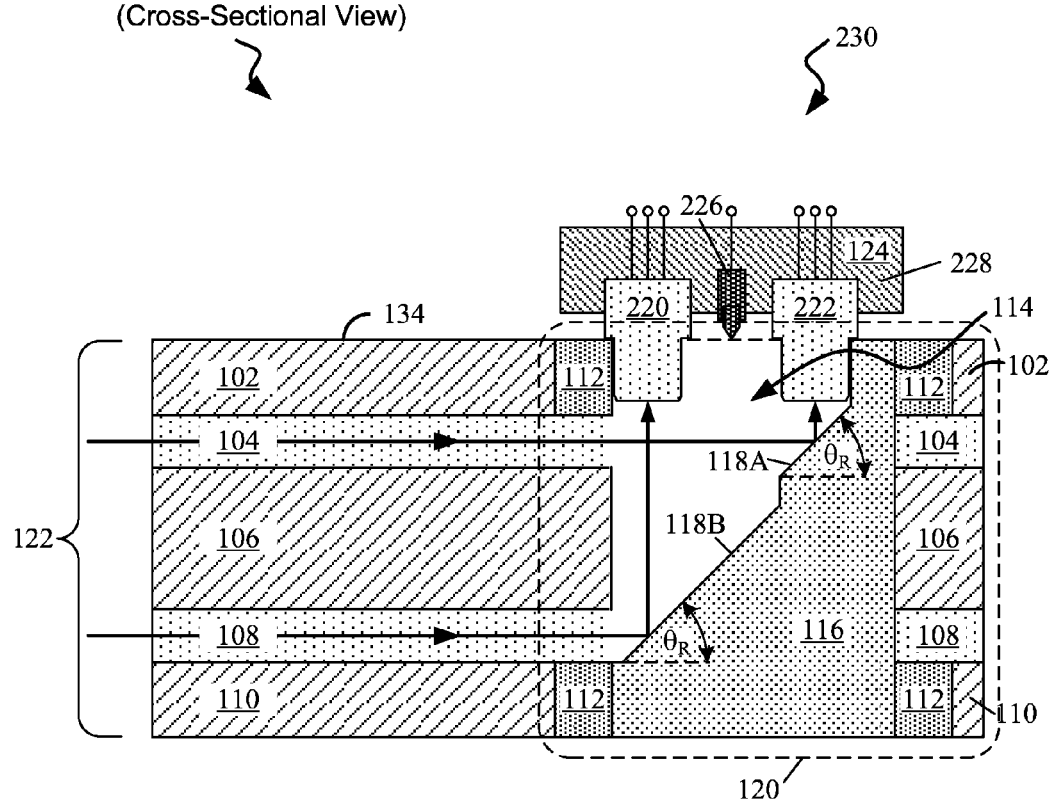
FIG. 2 depicts a cross-sectional view of an assembly including a PCB, an optical/electrical connector structure and a mating connector, according to embodiments.

FIG. 2 is a cross sectional view 200 of a printed circuit board 122 including an optical/electrical connector structure 120 and a mating connector 230, configured to transmit/receive optical signals to/from connector structure 120, according to embodiments consistent with FIG. 1.

In certain embodiments, the connector 230 may be configured to mate with connector structure 120 and to receive optical signals transmitted through an optical conductor layer (e.g., layer 104) of the PCB 122, and reflected off of a reflective surface (e.g., 118A) of connector structure 120. Connector 230 may be useful as a device which may receive and convert optical signals, transmitted within internal layers of PCB 122, into electrical signals which may be transmitted to other electronic devices. Connector 230 may also be useful in providing local access to related signals that are optically and electrically transmitted through adjacent signal transmission paths within PCB 122.

View 200 is a cross-section of an assembly including a PCB 122, an optical/electrical connector structure 120, and a mating connector 230, the assembly being sectioned along line A-A of view 150 (FIG. 1).

Connector 230 may include a connector body 124 physically attached to at least one optical module, e.g., 220, 222, and at least one compressible electronic contact 226. An alignment structure may be configured to align connector 230 to the opening of the via 114 on the first face 134 of the printed circuit board 122. For example, the position of, and distance between, optical modules 220, 222 in connector body 124 may allow both optical modules 220, 222 to be inserted into the opening of the via 114, with a dimensional tolerance between optical modules 220, 222 and the via opening 114 that is sufficiently small to ensure that optical modules 220, 222 are positioned to receive or transmit optical signals reflected from or off of reflective surfaces 118A, 118B. Other types of alignment structures are possible, including pins and corresponding holes, and frames, mounted to PCB 122, that include a recess to receive a connector such as connector 230. Connector body 124 may be fabricated from an electrically insulative material such as plastic, and may be held in place against PCB 122 with screws, a clip, latch or other fastening device.

In certain embodiments, optical modules 220, 222 may include a commercially available Receiver Optical Sub Assembly (ROSA), which may contain a photodiode and Trans-impedance Amplifier (TIA) integrated in a standard package. In certain embodiments, optical modules 220, 222 may include a commercially available Transmit Optical Sub Assembly (TOSA), which may contain one or more directly modulated lasers (DMLs) and an optical multiplexer, integrated in a standard package. In embodiments, ROSAs and TOSAs may be useful for serial data communication through transmission of optical signals at rates of up to 40 Gbps. Other types of optical modules may be used in connector 230.

Compressible electrical contacts, e.g., 226, may be used to establish an electrical connection to a signal carried on electrical signal transmission path 106A (FIG. 1, view 150), which may be electrically connected to electrically conductive material 116. Compressible electrical contacts may also be used to connect to a surface metal layer (e.g., 102) which may be connected to a ground or power supply node. According to embodiments, a compressible electrical contact may be configured to contact electrically conductive material (e.g., 116) when connector 230 is positioned against the first face 134 of PCB 122. A compressible electrical contact may also be configured to touch a surface-mount pad structure when the connector 230 is in a mating position with connector structure 120. In certain embodiments, the compressible electrical contact 226 may be a spring-loaded mechanism, and in certain embodiments the compressible electrical contact 226 may be a conductive elastomer. Other types of compressible electronic contacts 226 are considered.

Connector 230 may include electrical terminals that are connected to optical modules 220, 222 and compressible electrical contact 226. These electrical terminals may be connected to an electrical connector, cable (e.g., flex cable), or other electronic device or conductor, and may be useful in the transmission and reception of signals from and to optical modules 220, 222.

In certain embodiments, connector 230 may include an array of optical modules (e.g., 220) and compressible electrical contacts (e.g., 226), and may be integrated into an electronic module or other electronic device. In particular embodiments, a second PCB, oriented perpendicularly to PCB 122 may receive, through optically conductive layers within the second PCB, optical signals reflected off of reflective surfaces (e.g., 118A) of optically reflective material 116.

Figure 3:
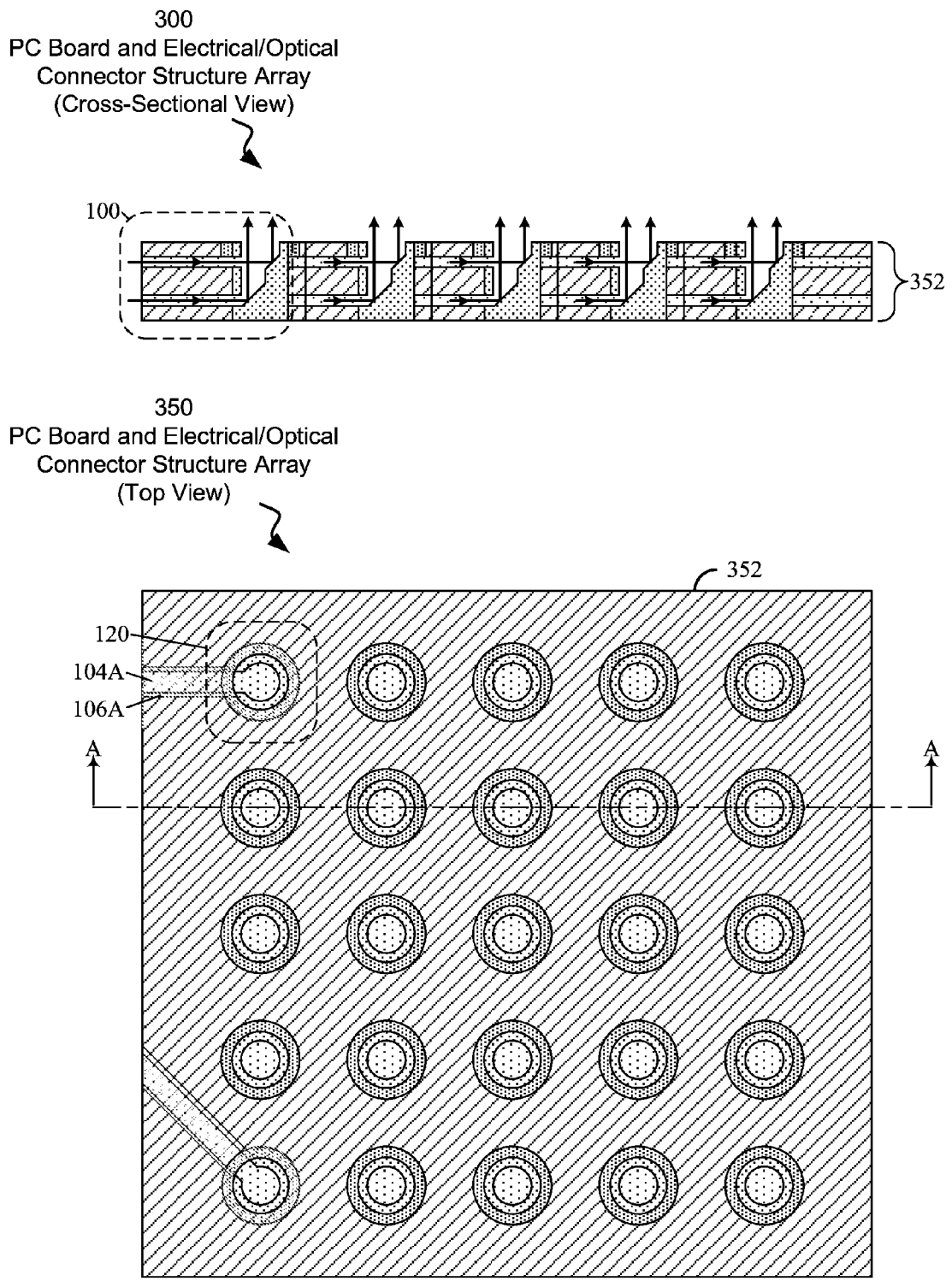
FIG. 3 includes a cross-sectional view and a top view depicting a printed circuit board including an array of optical/electrical connector structures, according to embodiments.

FIG. 3 is a cross sectional view 300 and a top view 350 depicting a printed circuit board (PCB) 352 including an array of optical/electrical connector structures 120, configured to interface with a mating connector such as 230, FIG. 2, according to embodiments consistent with the figures. In certain embodiments, the PCB 352 may be configured to transmit and receive a plurality of optical and electrical signals from/to a connector such as 230, FIG. 2, through an array of connector structures 120.

An array of optical/electrical connector structures 120 may be useful in providing compact, high bandwidth optical and electrical interconnections between a PCB (e.g., 352) and a connector, cable, electronic module, or other electronic device. The array of optical/electrical connector structures 120 may be particularly useful in providing access, on a face of a PCB, to optical and electrical signal transmission paths which may be formed on internal layers of a PCB. Related signals, e.g., a data or address bus or group of control signals may be accessed through adjacent or locally positioned connector structures 120.

View 300 is a cross-section of a PCB 352 including a plurality of optical/electrical connector structures 100 embedded within the PCB 352, the PCB 352 being sectioned along line A-A of view 350 (FIG. 3).

According to embodiments, PCB 352 (view 350) may have a plurality of optical signal transmission paths (consistent with 104A, FIG. 1) within a plurality of its internal layers. The layers of PCB 352 may contain a plurality of optical conductor layers consistent with 104, FIG. 1. PCB 352 may also contain a plurality of electrical signal transmission paths (consistent with 106A, FIG. 1), and a plurality of metal layers consistent with 106, FIG. 1. Connector structure 120 (view 350) depicts an associated optical signal transmission path 104A and associated electrical signal transmission path 106A. Optical signal transmission path 104A may be useful for optically connecting connector structure 120 with another connector structure on the PCB 352. Similarly, electrical signal transmission path 106A may be useful for electrically connecting connector structure 120 with another connector structure, or component on the PCB 352.

According to embodiments, an array of connector structures 120 may be compatible with existing PCB footprints for electronic components having an array of connections with standardized dimensions, such as ball grid array (BGA) or land grid array (LGA) modules. In certain embodiments, an array of connector structures 120 may include five rows and five columns, and in certain embodiments the array may include fifteen rows and fifteen columns of connector structures 120. In particular embodiments, the array may include thirty rows and thirty columns of connector structures 120. The number of rows and columns of connector structures 120 may be consistent with available electronic package footprints. In certain embodiments, connector structures 120 may be used in conjunction with capture pads (e.g., BGA or LGA pads), in an array configuration, on the surface of a PCB.

Figure 4:
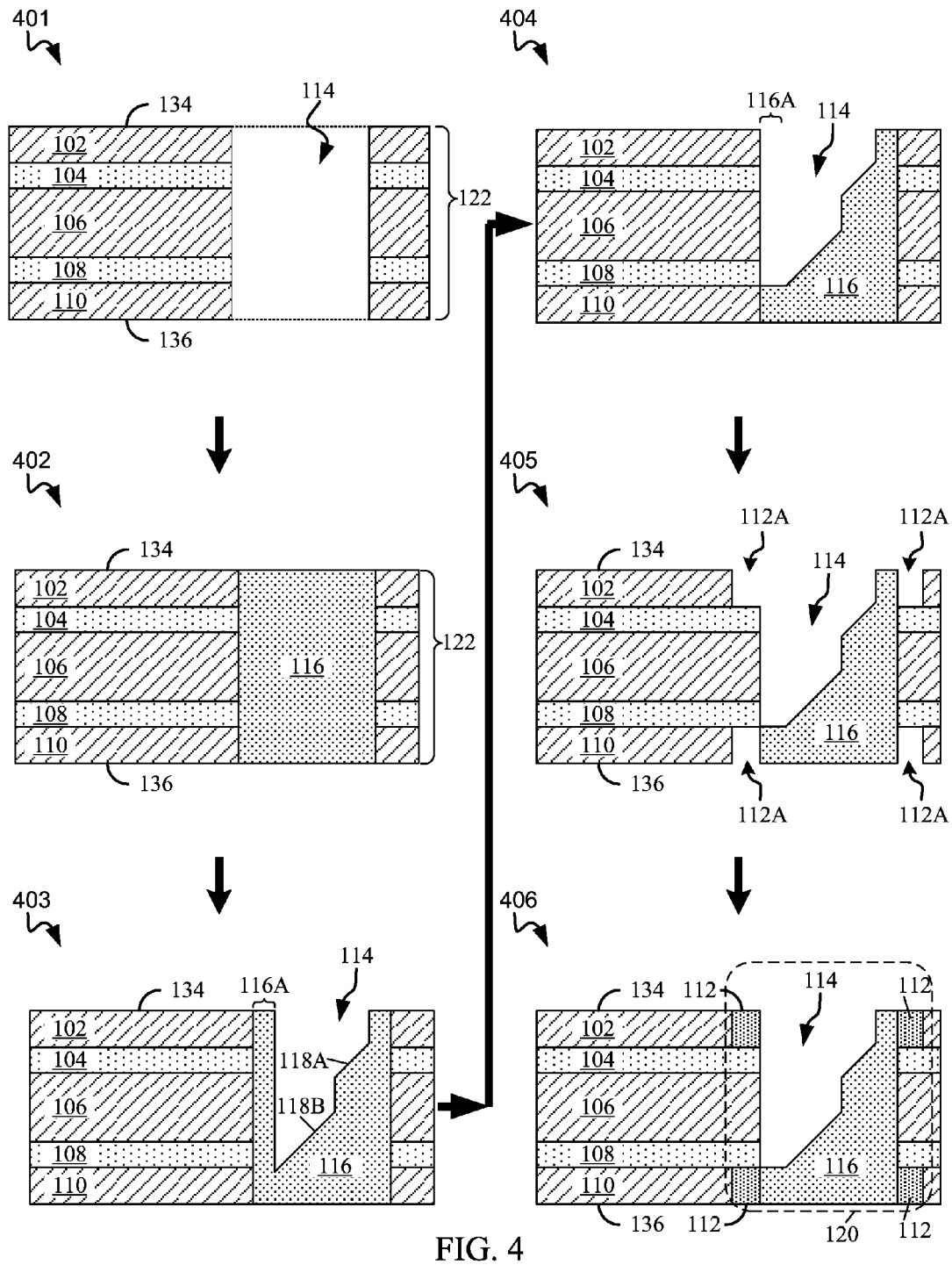
FIG. 4 includes six cross-sectional views illustrating the results of process steps for fabricating an optical/electrical connector structure, according to embodiments.

FIG. 4 includes six cross-sectional views 401-406, illustrating the results of a sequential set of process steps for fabricating an optical/electrical connector structure (e.g., 120, FIG. 1), according to embodiments of the present disclosure consistent with the figures. These views illustrate an example process; other views and steps may be possible. The results of one or more process steps may be depicted in each view. For example, a view may depict the results of depositing a dielectric material (e.g., 112), which may include related deposition, curing and subsequent leveling steps. Processing steps associated with views 401 through 406 may include, but are not limited to, metallic seeding, electroplating, material removal/laser ablation, etching, and material deposition.

The progression depicted in views 401 through 406 begins with a PCB 122 with a via 114 (view 401) and ends with PCB with an embedded connector structure 120 (view 406). For simplicity of illustration, completed structures are generally shown in the views as having rectangular cross-sectional profiles, with surfaces orthogonal to each other. This depiction, however, is not limiting; structures may be of any suitable shape, size and profile, in accordance with specific design criteria, lithographic and manufacturing process limitations and tolerances for a given application. For example, corners shown as having right angles may be rounded, surfaces may have a non-orthogonal relative orientation, and relative dimensional ratios may vary from those depicted in the figures. Views 401 through 406 illustrate the process of manufacturing a single optical/electrical connector structure 120, however, in embodiments, a plurality of connector structures may be simultaneously manufactured within the same PCB 122.

View 401 depicts a printed circuit board (PCB) 122, having a generally planar shape, a via 114, top surface 134 and bottom surface 136. The PCB 122 may include metal layers 102, 106 and 110 and first and second optical conductor layers 104, 108, respectively. Optical conductor layers 104, 108 may include optical signal transmission paths. In certain embodiments, outer metal layers 102 and 110 may be used as ground or power supply layers, and metal layer 106 may be used for conducting electrical signals, through an included electrical signal transmission path.

Via 114 may have a cylindrical shape, and a diameter, depth and aspect ratio consistent with via dimensions for a particular PCB technology. Via 114 may intersect a first optical signal transmission path on optical conductor layer 104 and an electrical signal transmission path on metal layer 106.

View 402 depicts the result of depositing an electrically conductive and optically reflective material 116 in the via opening 114. The electrically conductive and optically reflective material 116 may be copper, copper alloys or another metal or material. The material may be sufficiently electrically conductive and optically reflective to conduct electrical signals from an internal metal layer to a face 134 of the PCB, and reflect optical signals from an (internal) optical conductor layer, e.g., 104, 108, to an opening in via 114 at the face of the PCB 122, respectively. The via 114 may be seeded with a thin layer of copper, for example, and then electroplated until the via 114 is filled.

View 403 depicts the result of removing an inner portion of the electrically conductive and optically reflective material 116 to form reflective surfaces 118A, 118B. Surfaces 118A, 118B may have angles, relative to light transmitted by the optical signal transmission paths (in layers 104, 108), sufficient to reflect the light to an opening of the via 114 on the first face 134 of PCB 122. The inner portion of material 116 may be selectively removed by a process of laser ablation. A laser ablation process may use a large number of laser pulses (e.g., up to 30,000) of measured and controlled energy (e.g., in a range from 1 pJ to 20 pJ), and may be performed under low-pressure (e.g., 0.1 mbar) conditions in a vacuum chamber.

Following the removal of an inner portion of material 116, a circular perimeter portion of material 116 may remain, adjacent to the cylindrical wall of via 114. The circular perimeter portion of material 116 may include the outer portion 116A (see FIG. 1, view 150) of material 116, which may block optical signals from emerging from optically conductive layers 104, 108 into via 114.

View 404 depicts the result of selectively removing the outer portion 116A of material 116, by a process of laser ablation. Removing material in area 116A may enable optical signals to emerge from optically conductive layers 104, 108 into via 114, and be reflected off of reflective surfaces (e.g., 118A, 118B). Following removal of material in area 116A (see also FIG. 1, view 150), an electrical connection between material 116 and metal layer 106 may remain, which may be useful in conducting electrical signals between the connector structure 120, connected to material 116, and metal layer 106, which may contain electrical signal transmission paths.

View 405 depicts the result of removing metal (e.g., copper) from metal layers 102, 110, to create dielectric cavities 112A, adjacent to the via 114 on the first and second faces 134, 136 respectively of PCB 122. Dielectric cavities 112A may be useful around a perimeter of via 114 by insulating electrically conductive material 116 from metal layers 102 and 110. Dielectric cavity 112A may be useful as a receptacle for dielectric material.

View 406 depicts the result of depositing dielectric material 112 to replace electrically conductive material (e.g., copper) removed from metal layers 102, 110 adjacent to the via 114 on the first and second faces 134, 136 respectively, of PCB 122. Dielectric material 112 may electrically insulate material 116 from metal layers 102 and 110.

Specified and actual finished dimensions of structures depicted in views 401 through 406 may be generally constrained by design needs, manufacturing and process tolerances, and availability of materials having certain dimensions.

Figure 5:
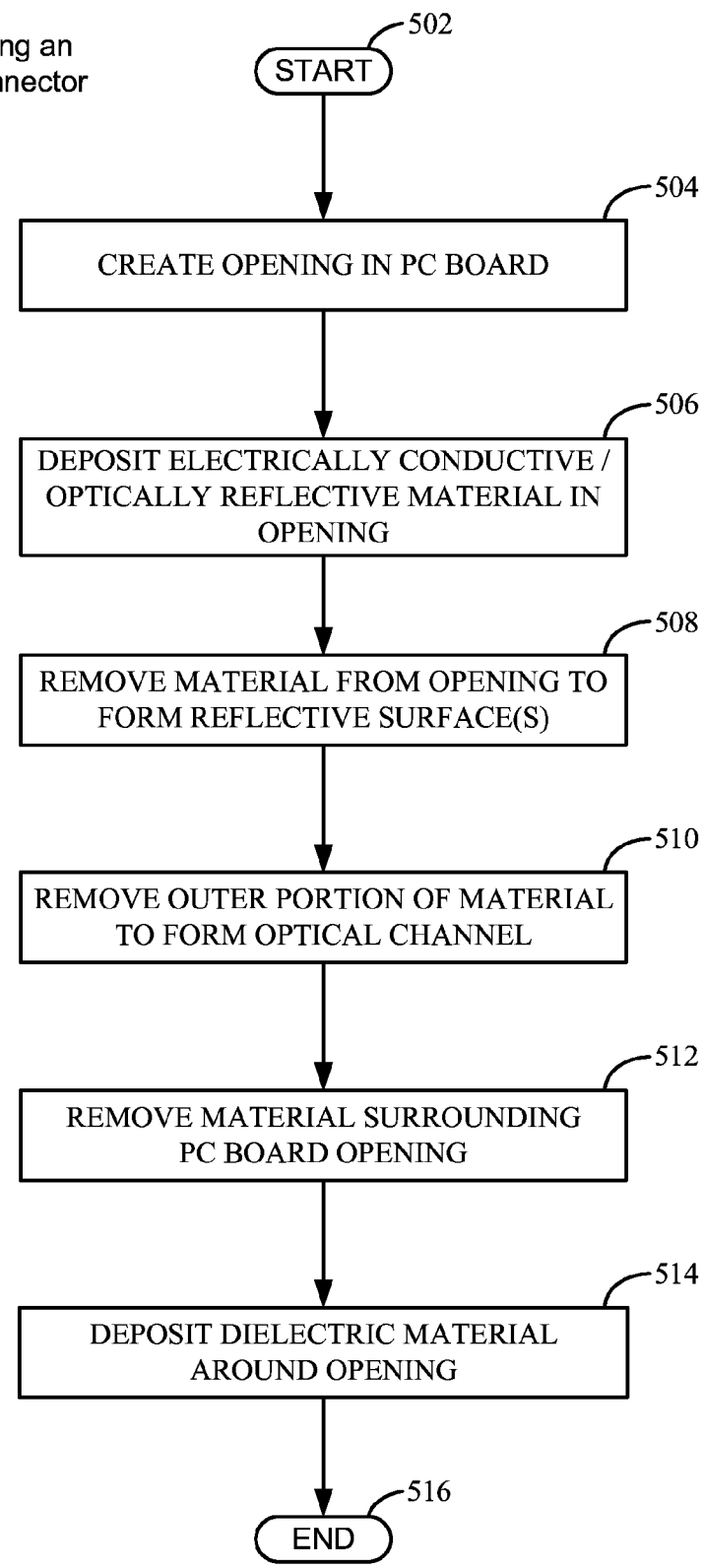
FIG. 5 is a flow diagram illustrating the steps for fabricating an optical/electrical connector structure, according to embodiments.

FIG. 5 is a flow diagram illustrating the steps for fabricating an optical/electrical connector structure, according to embodiments consistent with the figures. The method for fabricating an optical/electrical connector structure 500 may be useful for creating PCB surface-mount connector structures that are compatible with existing PCB material sets and technologies. The process 500 moves from start 502 to operation 504.

Operation 504 generally refers to the process steps that involve creating an opening (via) in a PCB, which may correspond to the view provided by view 401 (FIG. 4) and its associated description. Creating a via through mechanical or laser drilling may expose all internal layers of a PCB, which may be useful by providing access to signals transmitted on internal layers of the PCB. Once an opening (114, view 401) has been created in the PCB, the process moves to operation 506.

Operation 506 generally refers to the process steps that involve depositing material that is electrically conductive and optically reflective (116, view 402) in the via, which may correspond to view 402 (FIG. 4) and its associated description. In certain embodiments, following the filling operation, material 116 may be leveled to create top and bottom surfaces of material 116 that are substantially planar with the first face 134 and the second face 136 of the PCB (view 402, FIG. 4).

Once electrically conductive and optically reflective material has been deposited in the via, the process moves to operation 508.

Operation 508 generally refers to the process steps that involve forming one or more reflective surfaces by removing an inner portion of material 116 from the via 114, which may correspond to the view 403 (FIG. 4) and its associated description. A laser ablation process involving a controlled duration, energy, and wavelength of laser pulses used to evaporate material 116 from the via 114 may result in precise machining of material 116. Once the reflective surfaces have been formed, the process moves to operation 510.

Operation 510 generally refers to the process steps that involve removing an outer portion 116A of material 116 to form an optical channel into the via opening (114, FIG. 4) which may correspond to the view 404 (FIG. 4) and its associated description. A laser ablation process may be used to remove material 116A (see view 150, FIG. 1 and view 403, FIG. 4), and may, due to the short duration and limited overall material heating involved in the laser ablation process, be useful in preserving optical properties of optical conductor layers 104, 108 (FIG. 4). Once outer portion 116A of material 116 has been removed, the process moves to operation 512.

Operation 512 generally refers to the process steps that involve selectively removing metal from portions of metal layers 102, 110 (FIG. 4) that surround via opening 114 to create dielectric cavities 112A (FIG. 4), which may correspond to view 405 (FIG. 4) and its associated description. Removal of metal from metal layers 102, 110 may involve photolithographic, masking, and etching operations. Dielectric cavities 112A (FIG. 4) may be useful to contain a dielectric material which may insulate metal layers 102, 110 and associated signals from material 116. Once the metal surrounding via opening 114 has been selectively removed, the process moves to operation 514.

Operation 514 generally refers to the process steps that involve depositing a dielectric material 112 (FIG. 4) into the dielectric cavities 112A (FIG. 4) created in operation 512, which may correspond to view 406 (FIG. 4) and its associated description. Dielectric material 112 may be deposited into dielectric cavities 112A (FIG. 4) using one or more of a variety of processes, including but not limited to hot melt extrusion, insert molding and spin coating. Hot melt extrusion, for example, may involve forcing dielectric material under pressure through a nozzle into the optical dielectric cavities 112A (FIG. 4. Dielectric material 112 may be in a liquid, gel, or other viscous state while being deposited. Once the dielectric material has been deposited in the dielectric cavities 112A (FIG. 4), the process 500 may end at block 516.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method for forming a system for use with optical and electrical signaling in a printed circuit board that includes a plurality of layers vertically stacked between a first face and a second face, a first optical signal transmission path within a first internal layer of the plurality of layers and an electrical signal transmission path, the method comprising:
    creating an opening in the printed circuit board that intersects the first optical signal transmission path and the electrical signal transmission path;
    depositing an electrically conductive and optically reflective material in the opening;
    removing an inner portion of the electrically conductive and optically reflective material to form a reflective surface that is configured to reflect light between the optical signal transmission path and an opening of the via on the first face; and
    removing an outer portion of the electrically conductive material from the via to allow light from the optical signal transmission path to reach the reflective surface, while leaving a portion of the conductive material in the via in contact with the electrical signal transmission path.

2. The method of claim 1, wherein removing an inner portion of the electrically conductive material and removing an outer portion of the electrically conductive material includes laser ablation.

3. The method of claim 1, wherein the reflective surface has an angle, relative to light transmitted by the optical signal transmission path, sufficient to reflect the light to an opening of the via on the first face.

4. The method of claim 1, further comprising removing electrically conductive material adjacent to the via on the first face from an outer layer of the plurality of layers.

5. The method of claim 4, further comprising depositing dielectric material to replace electrically conductive material removed from a location adjacent to the via on the first face.

* * * * *